United States Patent [19]

Maskalick et al.

[11] Patent Number: 4,847,172
[45] Date of Patent: Jul. 11, 1989

[54] LOW RESISTANCE FUEL ELECTRODES

[75] Inventors: Nichols J. Maskalick, Pittsburgh; George R. Folser, Lower Burrell, both of Pa.

[73] Assignee: Westinghouse Electric Corp., Pittsburgh, Pa.

[21] Appl. No.: 158,815

[22] Filed: Feb. 22, 1988

[51] Int. Cl.$^4$ .............................................. H01M 8/10
[52] U.S. Cl. ........................................ 429/30; 429/31
[58] Field of Search ................... 429/31, 30, 44, 40; 29/623.1, 623.5; 427/115

[56] References Cited

U.S. PATENT DOCUMENTS

| | | | |
|---|---|---|---|
| 3,835,514 | 9/1974 | Pollack | 29/2 |
| 3,895,960 | 7/1975 | Brown et al. | 136/36 |
| 4,395,468 | 7/1983 | Isenberg | 429/31 |
| 4,447,509 | 5/1984 | Maskalick | 429/235 |
| 4,490,444 | 12/1984 | Isenberg | 429/31 |
| 4,582,766 | 4/1986 | Isenberg et al. | 429/30 |
| 4,597,170 | 7/1986 | Jsenberg | 29/623.5 |
| 4,598,028 | 7/1986 | Rossing et al. | 429/30 |
| 4,609,562 | 9/1986 | Isenberg et al. | 427/8 |
| 4,702,971 | 10/1987 | Jsenberg | 429/31 |

Primary Examiner—Anthony Skapars
Attorney, Agent, or Firm—Daniel P. Cillop

[57] ABSTRACT

An electrode 6 bonded to a solid, ion conducting electrolyte 5 is made, where the electrode 6 comprises a ceramic metal oxide 18, metal particles 17, and heat stable metal fibers 19, where the metal fibers provide a matrix structure for the electrode. The electrolyte 5 can be bonded to an air electrode cathode 4, to provide an electrochemical cell 2, preferably of tubular design.

12 Claims, 1 Drawing Sheet

LOW RESISTANCE FUEL ELECTRODES

GOVERNMENT CONTRACT

The Government of the United States of America has rights in this invention pursuant to Contract No. BNL 585847-S, awarded by the U.S. Department of Energy.

BACKGROUND OF THE INVENTION

1. Field of the Invention

The present invention relates to low resistance fuel electrode anodes for solid oxide electrochemical cells.

2. Description of the Prior Art

High temperature, solid oxide electrolyte, electrochemical cell configurations, and generating apparatus are well known in the art, and are taught by Isenberg, in U.S. Pat. Nos. 4,395,468 and 4,490,444. The standard fuel electrode anode material used is porous nickel-zirconia cermet. A method and apparatus that can be used to form such cermet anodes are taught by Isenberg, in U.S. Pat. No. 4,597,170 and by Isenberg et al., in U.S. Pat. No. 4,609,562, respectively.

Improvements to the cermet anode have been to make them more electrochemically active, by oxidizing and then reducing a portion of the metal particles held in place by a ceramic skeletal formation, which is fissured during oxidation, as taught by Isenberg et al., in U.S. Pat. No. 4,582,766. However, in most instances, it is impossible to get the metal particles compacted enough so that there is complete electronic interconnection between the metal particles. Additional improvements to the cermet anode have been made to make them more sulfur tolerant, by covering the ceramic skeleton and metal particles with a coating of ceria and urania based oxides, as taught by Isenberg, in U.S. Pat. No. 4,702,971. None of these improvements, however, address lowering the electronic resistance of the anode. What is needed is a simple and inexpensive way to lower both cermet fuel electrode resistance, and overall cell resistance.

3. Object of the Invention

It is an object of this invention to provide a new fuel electrode anode structure which will have low electronic resistance and impart an overall lower cell resistance.

SUMMARY OF THE INVENTION

Accordingly, the invention resides in a cermet electrode, comprising ceramic metal oxide and metal particles, bonded to a solid oxygen ion conducting electrolyte, where the cermet electrode is characterized in that heat stable metal fibers, preferably nickel fibers, are disposed within the electrode structure. The electrolyte can be disposed on top of and bonded to an air electrode cathode, to provide an electrochemical cell, preferably of tubular design.

Further according to the invention, is a method of bonding a cermet electrode on a solid oxygen ion conducting electrolyte, by first forming a layer of metal particles in a matrix of heat stable metal fibers on a first surface of the electrolyte, applying a source of oxygen to a second surface of the electrolyte, applying a metal halide vapor to the first surface of the electrolyte, and heating the electrolyte to a temperature sufficient to induce oxygen to diffuse through the electrolyte and react with the metal halide, so that a metal oxide skeletal structure grows partially around the metal particles all within an enclosing heat stable metal fiber matrix, which matrix helps to electronically interconnect metal particles. In the article and method, the metal fibers dramatically increase electronic interconnection between the metal particles, such as to lower the resistance of the entire cell.

The preferred electrolyte and ceramic metal oxide used in the cermet electrode is stabilized zirconia, and the preferred metal conductor particles are nickel particles. The preferred heat stable metal fibers are in felt form, providing a porous, interlocking fibrous body which may be bonded at fiber contact points with other fibers, and with nickel particles. The term "heat stable metal fibers", as used herein means metal fibers that are chemically stable in the fuel atmosphere (will not oxidize to any substantial degree) at the operating temperature of the generator, and that are thermally stable (will not melt) at the approximate 800° C. to 1000° C. operating temperature of the generator apparatus. Examples include iron, cobalt, copper, gold, platinum, preferably nickel, and alloys and mixtures thereof. The heat stable metal fibers provide a matrix which contains the metal particle—ceramic metal oxide skeletal structure. The use of a metal fiber felt reduces the anode resistance, substantially reduces the overall cell electronic resistance, and also helps prevent dripping and loss of anode metal particle slurry during formation of the fuel electrode.

BRIEF DESCRIPTION OF THE DRAWINGS

The invention will become more apparent by reading the following detailed description in conjunction with the drawings, which are shown by way of example only, wherein.

DESCRIPTION OF THE PREFERRED EMBODIMENTS

Figure 1:
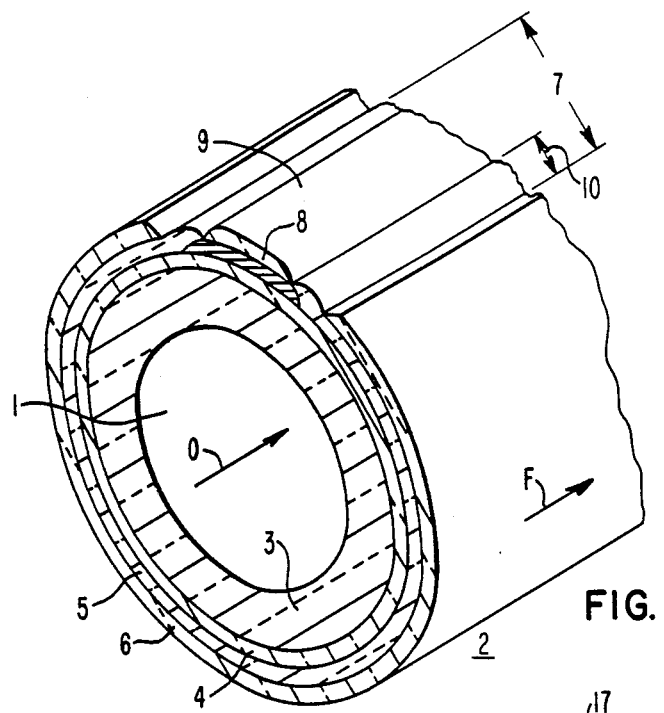
FIG. 1 is an isometric view in section of one embodiment of a tubular electrochemical cell according to this invention.

Referring now to the Drawings, FIG. 1 shows a tubular, solid oxide electrolyte, electrochemical cell, such as a fuel cell, with air or oxygen flowing through the center 1 of the cell 2. The air (oxygen) permeates through optional porous support tube 3 to air electrode 4, where oxygen is converted to oxygen ions. The oxygen ions are conducted through electrolyte 5 to cermet fuel electrode anode 6, where they react with fuel, F, such as $H_2$, $CO$, $CH_4$, etc., to generate electricity. As can be seen, the fuel electrode in this configuration is an exterior electrode, where the electrolyte is in tubular form and in contact with an interior air electrode.

Also shown in FIG. 1 is a longitudinal space 7 containing an interconnection 8 for making electrical connections from the underlying air electrode to the fuel electrode 6 of an adjacent cell tube (not shown). Electronically insulating gap 10 is also shown. A metal or fuel electrode type of material 9 may be coated over interconnection 8. A detailed description of the general operation of the solid oxide fuel cell, along with appropriate description of useful support, air electrode, and interconnection materials, can be found in U.S. Pat. No.

4,490,444, assigned to the assignee of this invention, herein incorporated by reference.

The electrochemical cell and electrolyte 5 can have a variety of shapes, but the preferred shape is tubular, as that configuration is the most useful for solid oxide electrochemical cells. The most useful air electrode cathodes are made of doped and undoped oxides or mixtures of oxides in the perovskite family, such as $LaMnO_3$, $CaMnO_3$, $LaNiO_3$, $LaCoO_3$, $LaCrO_3$, doped indium oxide, $In_2O_3$, and the like. The electrolyte material 5 is typically an oxide having a fluorite structure or a mixed oxide in the perovskite family, but other simple oxides, mixed oxides, or mixtures of simple and mixed oxides can be used. The preferred electrolyte material is stabilized zirconia, a readily available commercial material. The zirconia may be stabilized, i.e., doped, with a number of elements, as is well known in the art, but rare earth element stabilized zirconia, specifically, yttria stabilized zirconia, is preferred, as it has excellent oxygen ion mobility. A preferred composition is $(ZrO_2)_{0.90}(Y_2O_3)_{0.10}$ as that material works well in solid oxide electrochemical cells. Other mixed oxides can be used including yttrium doped thorium oxide. The method of this invention is applicable to oxide layers which transfer oxygen in any form including monoatomic oxygen as well as ionic oxygen.

Figure 2:
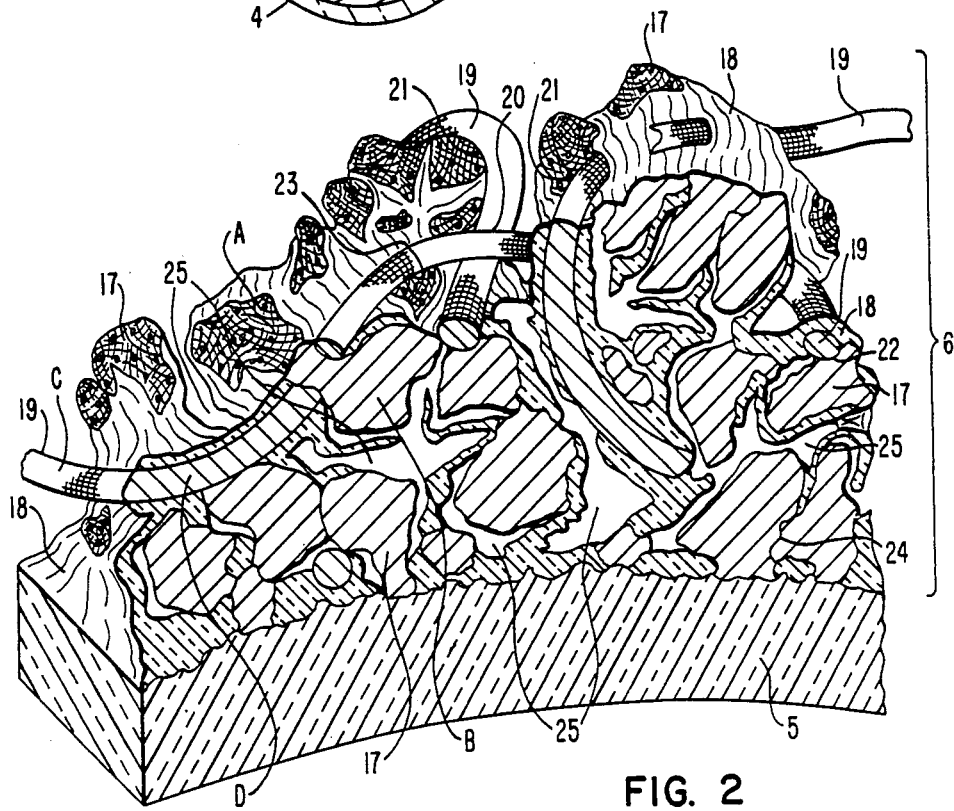
FIG 2, which best illustrates the invention, is a simplified isometric illustration, partly in section, showing the porous fuel electrode anode of this invention with nickel fibers disposed within the electrode as a matrix structure, all disposed on top of a solid electrolyte substrate.

The cermet fuel electrode anode 6, is shown in a simplified view in FIG. 2, where the cross-section ideally shows several metal fibers 19. For sake of clarity, the metal fibers 19 are all shown with circular cross-sections, whereas they will in fact, have a wide variety of irregular cross-sections. The solid electrolyte substrate 5 is shown supporting metal particles 17, partly covered or completely enclosed, and bound by a ceramic oxide skeletal structure 18 attached to and growing from the electrolyte 5. The exterior portions of metal particles are shown stippled while the interior portions are shown hatched as metal.

The partly covered or completely enclosed metal particles are connected by and held within a heat stable metal fiber matrix, preferably of long nickel fibers 19, which may contact each other at cross-over points 20. Thus, the heat stable metal fibers 19 are disposed within the fuel electrode structure 6. The long metal fibers usually provide a random directional fiber matrix as shown. The metal fibers are embedded in and run through portions of the skeletal structure 18. The metal fibers 19 are preferably in the form of a felt, and may be metal-to-metal diffusion bonded together at cross-over points 20 or at points of contact with the nickel metal particles.

It should be recognized that FIG. 2 shows an initial, frontal, cross-sectional view that blends into a three dimensional view. Thus, three dimensional particle A (stippled) is shown to extend into the structure to become cross-sectional particle B (hatched as metal), the metal fiber being cut for the sake of simplicity at that point, just as external metal fiber C extends into the structure to become cross-sectional metal fiber D.

The metal fibers 19 can be disposed within a part of, or all of the thickness of fuel electrode structure 6. The combination of heat stable metal fibers plus metal particles provide outstanding electrical conductivity and a dramatic reduction in fuel electrode and overall cell resistance. As can be seen in FIG. 2, the skeleton 18 grows over parts of the metal particles 17 and metal fibers 19 as a thin film, which is thicker near the electrolyte 5. The particles are thus in what can be characterized as a double matrix of ceramic oxide skeleton and long heat stable metal fibers, where the metal fibers and metal particles are in intimate and bonded contact at a great many points in the fuel electrode structure, as at points 21.

As shown, a heat stable metal fiber may make contact with a portion of a metal particle where both are covered with the skeleton structure, as at point 22, and then the metal fiber may surface and contact an exterior portion of an exposed metal particle, as at point 23, all adding to the electronic conductivity of the anode 6. The long heat stable metal fiber matrix thus encloses and electronically interconnects metal particles. The metal particles also contact each other at many points, as at point 24. A large number of voids or pores, shown as 25 are also present in the anode structure.

A preferred fuel electrode anode thickness for this invention is from 100 microns to 300 microns 0.10 mm to 0.30 mm) preferably from 100 microns to 200 microns (0.10 mm to 0.20 mm). Nickel, cobalt, and alloys and mixtures thereof can be used as the metal particles 17 embedded within the skeletal and matrix structure of fuel electrode structure 6. The metal particles will have diameters or dimensions roughly corresponding to diameters of from 1 micron to 100 microns (0.001 mm to 0.10 mm), preferably from 1 micron to 25 microns (0.001 mm to 0.025 mm). The nickel fibers are from 1 mm to 15 mm long and can have a cross-sectional dimension corresponding to diameters of from 0.005 mm to 0.05 mm, and are thus very long in respect to their diameter. The fibers can be made by well known techniques of machining foil, bar stock or wire. Nickel fibers are preferred in this invention. However other suitable materials that have melting points above approximately 1000° C. and are chemically stable (will not oxidize to any substantial degree) in a fuel atmosphere at such temperatures can be used. Other useful heat stable metals include iron, cobalt, copper, gold and platinum, and alloys and mixtures thereof and with nickel.

Preferably, the heat stable metal fibers used in this invention will be in the form of a metal felt from 70% to 95% porous (5% to 30% of theoretical density) and from 0.005 mm to 0.025 mm thick. In the method of making the porous felt, metal fibers can be felted or laid down by any appropriate means, in a simple, random, intermingled orientation or at some specified angle, as shown, for example in U.S. Pat. Nos. 3,895.960 and 3,835,514, respectively, and then, optionally, diffusion bonded together. Diffusion bonding is for a time sufficient to allow interdiffusion of atoms across the fiber interface where the fibers contact, without any melting. After diffusion bonding, the bonded fibrous body can be easily handled, acquiring strength and structural integrity.

The metal particles 17 may be applied to contact the electrolyte as a powder layer in many different ways, including slurry dipping and spraying. Another method of application is a tape transfer technique, which is useful because of ease of mass fabrication, and uniformity in thickness and porosity. In most instances, it is impossible, however to attain complete and intimate contact of all the metal particles without use of high pressure isostatic press techniques, which would remove porosity, and decrease the gas permeability of the electrode layer. This invention helps provide such needed intimate contact without decreasing desired porosity.

The material which binds the conductor metal particles 17 to the electrolyte 5, and provides a skeleton 18 partly or completely embedding the conductor metal particles and heat stable metal fibers 19, can be applied by vapor deposition and formed from two reactants. The first reactant can be water vapor, carbon dioxide or oxygen itself, and the second reactant can be a metal halide, preferably zirconium tetrachloride, plus the halide of a stabilizing element, such as yttrium chloride. The skeletal binding material is preferably selected to be the same material as the electrolyte (or the same material modified by doping) so that a good bond forms between the binding material and the electrolyte and there is a good thermal match between the two materials. The preferred skeleton binding material 18 is yttria stabilized zirconia although a wide variety of ceramic metal oxides that are compatible with the electrolyte can be used.

The skeleton structure, when deposited by vapor deposition, has been found to grow around the metal particles. In order to form the metal particle embedded skeleton structure, a coating of the metal powder layer is applied to one surface of the solid oxide electrolyte. The metal particles can be applied first, followed by metal felt application, and then addition of more metal particles to fill the metal felt matrix. In another manner, metal felt can be applied directly to the electrolyte, followed by metal particle slurry impregnation of the metal felt matrix. In this last method, the slurry must be of low enough viscosity to completely penetrate the metal fiber matrix to the electrolyte surface. The metal particles can be applied in a liquid carrier, such as 5 wt. % aqueous polyvinyl alcohol, where solids content can vary from 30 wt. % to 70 wt. %.

After application of the metal particles in a matrix of metal fibers to a first surface of the electrolyte, a source of oxygen is applied to the second surface of the electrolyte, while a metal halide vapor is applied to the first, metal particle side. The electrolyte is heated to a temperature sufficient to vaporize any liquid carrier present and to induce oxygen to diffuse through the electrolyte and react with the metal halide vapor, causing a skeletal structure or coating to grow partly around or embed the metal particles, all within the nickel fiber matrix, to bond the particles and fibers to the electrolyte layer. This heating step also sinters contacting metal particles as well as contacting metal fibers together, to help develop good conductivity. The basic method is described in greater detail in U.S. Pat. No. 4,597,170, assigned to the assignee of this invention, herein incorporated by reference.

Electrochemically active sites in solid state electrochemical cells are where the reactant, electrolyte and electrode interface. These electrochemically active sites are where the fuel gas, is capable of combining with oxygen ions and where electron transfers can take place to generate an electric current. By using heat stable metal fibers in addition to metal particles, additional active sites are provided.

While the electrodes of this invention are primarily useful in solid oxide fuel cells, they can also be used as electrodes for solid state hydrolyzers and gas sensors. The invention will now be illustrated with reference to the following example.

EXAMPLE

A tubular cell, containing, in superimposed relationship, a porous support of calcia stabilized zirconia, an air electrode cathode of doped lanthanum manganite, and a dense electrolyte made of yttria stabilized zirconia, was constructed, and was similar to the first three layers of FIG. 1. The top electrolyte surface was then masked with polytetrafluoroethylene tape at the longitudinal interconnection space (shown as 7 on FIG. 1). the top of the electrolyte was dipped into a fluid slurry of nickel particle powder, of approximate 1 micron to 25 micron diameter, in 5 wt. % aqueous polyvinyl alcohol carrier-bonding agent. The solids content of the slurry was approximately 50 wt. %. A deposit of nickel particles on the electrolyte surface, approximately 0.01 gram/sq.cm. to 0.02 gram/sq.cm., was coated onto the unmasked portion of the electrolyte.

A 90% porous, nickel fiber felt, having diffusion bonded fibers approximately 3 mm to 15 mm long, and approximately 0.01 mm to 0.05 mm in diameter, was then applied on top of the nickel powder slurry, so that the nickel powder slurry penetrated and impregnated the bottom portion of the nickel fiber matrix. The felt thickness was approximately 0.075 mm thick. The felt provided approximately 0.01 gram/sq.cm. to 0.02 gram/sq. cm. of nickel fiber. The cell was again dipped into the same nickel particle powder slurry described previously to completely impregnate the nickel fiber matrix and provide an additional 0.10 gram/sq.cm. of nickel particles. The slurry was then dried. During drying very little nickel slurry was lost by dripping due to the nickel felt acting to contain the slurry.

The masking was then removed and the thus processed tube was subjected to an electric vapor deposition technique described previously, according to the teachings of U.S. Pat. No. 4,597,170. Oxygen was passed through the inside of the tube and a mixture of vapors containing zirconium tetrachloride and yttrium chloride were used on the outside of the tube. The temperature was approximately 1,200° C. The reaction was continued for about 10 minutes and then the tube was slowly cooled. By a similar process, a similar control sample tube was made except that no nickel fiber felt was used on top of the electrolyte. There, the slurry was applied in a single painting operation give the same content of nickel powder per square centimeter of electrolyte surface.

After vapor deposition microscopic examination of the electrodes showed that a skeleton of yttria stabilized zirconia had grown between the nickel particles, and also around the nickel fibers in the fiber containing electrode, to provide cermet anode structures about 0.15 mm thick, and about 35% to 45% porous. These cells were then tested for resistance and the results are given below in the Table:

TABLE

| Cell Sample | | Cell Resistance at 1000° C. |
|---|---|---|
| Ni particles and reinforcing zirconia in a Ni fiber matrix as anode | No. 1 | 0.41 |
| | No. 2 | 0.40 |
| Ni particles and reinforcing zirconia as anode* | No. 3 | 0.63 |

*Comparative, control sample standard cell.

As can be seen, total cell resistance was dramatically lowered by approximately 34%, i.e., (0.63−0.41)/0.63.

We claim:

1. A gas permeable electrode comprising ceramic metal oxide and metal particles bonded to a solid, ion conducting electrolyte, the improvement characterized in that heat stable metal fibers are disposed within the electrode structure as an interlocking matrix enclosing the metal particles and providing contact points between the metal fibers themselves and between the metal fibers and the metal particles, to form a porous electrode structure having extensive electronic interconnection between the metal particles.

2. The electrode of claim 1, where the ceramic metal oxide in the electrode is in the form of a skeletal structure which binds the metal particles.

3. The electrode of claim 1, where the electrolyte is a ceramic metal oxide.

4. The electrode of claim 1, where the metal particles are selected from the group consisting of nickel, cobalt, their alloys, and mixtures thereof.

5. The electrode of claim 1, where the electrode is also bonded to an air electrode cathode.

6. The electrode of claim 1, where the heat stable metal fibers are from 1 mm to 15 mm long, have a cross-sectional dimension corresponding to diameters of from 0.005 mm to 0.05 mm, and are nickel fibers, and where the electrode structure is about 35% to 45% porous.

7. A tubular electrochemical cell containing an exterior, gas permeable electrode bonded to the exterior of a tubular, solid, oxygen ion conducting electrolyte where the electrolyte is also in contact with an interior electrode, said exterior, gas permeable electrode comprising metal particles partly embedded in a skeletal structure of a ceramic metal oxide, the improvement characterized in that heat stable metal fibers are disposed within the exterior electrode structure as an interlocking matrix enclosing the metal particles and providing contact points between the metal fibers themselves and between the metal fibers and the metal particles, to form a porous electrode structure having extensive electronic interconnection between the metal particles.

8. The electrochemical cell of claim 7, where the electrolyte is a ceramic metal oxide and the interior electrode is an air electrode cathode.

9. The electrochemical cell of claim 7, where the metal particles are selected from the group consisting of nickel, cobalt, their alloys, and mixtures thereof.

10. The electrochemical cell of claim 7, where the heat stable metal fibers are from 1 mm to 15 mm long, have a cross-sectional dimension corresponding to diameters of from 0.005 mm to 0.05 mm, and are nickel fibers, and where the exterior electrode structure is about 35% to 45% porous.

11. The electrode of claim 1, where the heat stable metal fibers are selected from the group consisting of iron, cobalt, copper, gold, platinum, nickel, and mixtures thereof.

12. The electrochemical cell of claim 7, where the heat stable metal fibers are selected from the group consisting of iron, cobalt, copper, gold, platinum, nickel, and mixtures thereof.

* * * * *